United States Patent [19]

Rudov

[11] Patent Number: 4,943,433
[45] Date of Patent: Jul. 24, 1990

[54] PHARMACOLOGICAL/COSMETIC PREPARATION

[76] Inventor: David Rudov, 6 Tracey Crescent, Brighton, Victoria, 3186, Australia

[21] Appl. No.: 126,603

[22] Filed: Nov. 30, 1987

[30] Foreign Application Priority Data

Dec. 3, 1986 [AU] Australia ............................... PH9306
Sep. 23, 1987 [AU] Australia ............................... PI4530

[51] Int. Cl.$^5$ ............................................. A61K 35/78
[52] U.S. Cl. .................................. 424/195.1; 514/474; 514/725
[58] Field of Search .................... 424/195.1; 514/474, 514/725

[56] References Cited

U.S. PATENT DOCUMENTS

| | | | |
|---|---|---|---|
| 1,346,132 | 7/1920 | Matsuura | 424/195.1 |
| 2,229,684 | 1/1941 | Supplee et al. | 424/195.1 |
| 2,876,164 | 3/1959 | Wershaw | 424/195.1 |
| 2,992,159 | 7/1961 | Kahn | 424/195.1 |
| 3,247,065 | 4/1966 | Koff | 514/474 |
| 3,787,591 | 1/1974 | Hagiwara | 424/195.1 |
| 3,878,197 | 4/1975 | Maret | 424/195.1 |
| 4,670,263 | 6/1987 | Noorlander | 424/195.1 |
| 4,829,082 | 5/1989 | Shinkai et al. | 514/725 |

FOREIGN PATENT DOCUMENTS

| | | | |
|---|---|---|---|
| 1591652 | 6/1970 | France | 424/195.1 |
| 91108 | 8/1978 | Japan | 424/195.1 |
| 1427253 | 3/1976 | United Kingdom | 424/195.1 |
| 2095553 | 7/1982 | United Kingdom | 424/195.1 |

*Primary Examiner*—William R. Dixon, Jr.
*Assistant Examiner*—E. McAvoy
*Attorney, Agent, or Firm*—Ladas & Parry

[57] ABSTRACT

A pharmacologically effective or cosmetic substance for external application to treat e.g. acne, pimples, ulcers, cold sores. The substance includes an extract from plants of the grass family of plants particularly cereals, the extract including juice from green components of the plants at the unjointed stage. The extract is carried in a pharmaceutically acceptable aqueous carrier or excipient, the carrier preserving the extract against deterioration and being capable of at least partial absorption by tissues so as to carry the extract to sub-surface tissues. An anti-microbial agent is included. The substance may comprise ascorbic acid and beta-carotene, both present in the range 0.1 to 10 mg per gram of the substance. Biotin, trypsin and chlorophyll are also present.

10 Claims, No Drawings

PHARMACOLOGICAL/COSMETIC PREPARATION

This invention relates to substances and processes for cosmetic or medicinal treatment.

It is known to extract the juice of cereal grasses and to drink this juice as a source of dietary nutrients. The juice can be freshly extracted, previously frozen, or reconstituted juice from dehydrated cereal grass extract. Dehydrated extract from cereal grass leaves has been pressed into tablets for direct consumption or incorporation into foods and beverages. However these extracts have not been effectively used for medicinal or cosmetic purposes.

It is an object of the present invention to provide a pharmacologically effective substance and a cosmetic substance and processes for manufacturing and using such substances.

According to a first aspect of the present invention there is provided a pharmacologically effective substance for external aPPlication, the substance including an extract from plants of the grass family of plants, the extract including juice from green components of the plants, the extract being carried in a pharmaceutically acceptable carrier or excipient, the carrier o preserving the extract against deterioration and being capable of at least partial absorption by tissues so as to carry the extract to sub-surface tissues.

The present invention also provides a cosmetic substance for external application the substance including the same extract and being carried in a cosmetic base carrier with the same general properties.

The present invention also provides a method of manufacturing a substance for external application to surface body tissues, the method comprising the steps of treating plants of the grass family of plants to yield an extract including juice from green components of the plants, and mixing the extract with an acceptable carrier or excipient, the carrier being active to preserve the extract against deterioration and being capable of at least partial absorption by tissues so as to carry the extract to sub-surface tissues.

It is believed that cereal plants are preferred, although other Gramineae family plants such as wild grasses for example may be used to yield the extract. Extracts from barley, wheat and rye have been found to be effective. The wheat may comprise Triticum vulgare or aestivum, T. durum, or T. compactum. Corn, rice, oats, maize, sorghum and millet may also be effective.

Preferably the extract is derived from the green leafy part of the plant, or at least principally from this part of the plant, although additional green parts such as stalk may be included together with parts such as root, seed, sprouted seed. The leaves of the plant are preferably treated to yield the extract before the plant reaches flowering or seed production stage of development. That is, the plant is at its unjointed or immature development stage.

The extraction is preferably carried out by squeezing, crushing and/or grinding processes, not by a cutting process.

The plant extract may be used in the form in which it is derived from the plants. However preferably the extract is concentrated before mixing with the carrier. Preferably substantially all the liquid content of the plant extract is removed. For example, the extracted plant matter may be dried, such as by spray drying to yield a powder for mixing with the carrier. The spray drying is preferably carried out at a temperature of about 50° C. and preferably below 60° C. Other possible stabilization processes for the juice include Partial concentration of the derived juice to provide a concentrated liquid, freeze drying of the derived juice, and blending the derived juice with a preserving agent forming an ingredient of the carrier.

Preferably the stabilization or mixing with the carrier or both is carried out within a short time and preferably within a matter of hours after extraction. Preferably this time is two hours.

In an alternative possibility the extract may be produced by firstly drying plant matter after which the dried material is comminuted to yield a powder which includes ingredients originally in the juice.

The carrier for the extract may be any suitable material such as a cream, lotion, oil, gel or powder. For example the carrier may comprise a vanishing cream which is intended to be absorbed through the skin when externally applied so as to thereby carry the plant extract into sub-cutaneous tissue. A water based or aqueous carrier capable of carrying water soluble ingredients to sub-surface tissues is preferred.

It is believed that the following base creams and ointments may be suitable carriers although the fifth and sixth possible carriers may be susceptible to cracking due to incompatability between the extract according to the present invention and the carrier.

(1) Chlorhexidine cream aqueous A.P.F. supplied by Sigma.
(2) Aqueous cream B.P. supplied by Sigma.
(3) Cetomacrogol cream (Sorbolene cream) aqueous A.P.F. 79 supplied by McGloin's.
(4) Simple ointment (white) B.P. supplied by Sigma.
(5) Cetrimide cream aqueous A.P.F. supplied by McGloin's.

Note:
A.P.F.=Australian Pharmacopoeia Formulae
B.P.=British Pharmacopoeia

Preferably the carrier includes an anti-microbial agent so as to kill or at least inhibit growth, reproduction or activity of contaminating organisms that may be present in the plant extract or may be introduced during production of the substance. Preferably the anti-microbial agent is an anti-bacterial agent. In addition or alternatively the agent may have anti-fungal and anti-yeast properties. The anti-microbial agent may be added to the substance during Production or may be present in the carrier if the carrier for example is a standard commercially available blend. The anti-microbial agent is preferably active to inhibit any o activity of organisms and thereby is operative to inhibit spoilage of the substance, e.g. spoilage of the product when being stored by the user or by a commercial outlet.

If the anti-microbial is not provided, it is preferred that the extract is substantially sterile when mixed with the carrier. The plants from which the extract is derived may be grown hydroponically for example under sterile conditions to prevent the introduction of micro-organisms at that stage. The subsequent harvesting and processing may also be carried out under sterile conditions.

It has been found that a suitable carrier is Cetomacrogol emulsion having a typical analysis (by weight):

| | |
|---|---|
| wax | 15% |
| paraffin liquid | 10% |

| | |
|---|---|
| paraffin soft white | 10% |
| Chlorocresol | 0.1% |
| propylene glycol | 5% |
| water | balance to 100 |

The Chlorocresol is an anti-bacterial agent which is effective as an anti-microbial agent as described above.

The Cetomacrogol emulsion is believed to be effective since the plant extract ingredients will be dissolved or suspended in the water component. The propylene glycol is a surface active agent enhancing emulsification. The fatty or oily ingredients enhance the texture for skin surface application. Sorbolene can be included as a stabilizing agent.

The ratio of the extract to the carrier may be anywhere within a large range of possible ratios. For example the ratio of base carrier to plant extract land other additives if provided) may be anywhere between 1 to 5 and 200 to 1 (by weight). A range of 1 to 30% by weight of extract is preferred. About 10% by weight of extract has been found effective.

In analyzing and testing substances according to the present invention it has been found that several ingredients of the substance are identifiable and are believed to be active. Therefore these ingredients may be synthetically manufactured or at least initially sourced in unblended form, whether or not originally derived from plant matter. These ingredients can be blended in order to produce a substance according to the second aspect of the invention, this substance being a mixture of ingredients in a pharmaceutically acceptable or cosmetic carrier.

According to the second aspect of the invention there is Provided a pharmacologically effective substance for external application, the substance comprising ascorbic acid and beta-carotene in a pharmaceutically acceptable carrier or excipient, the carrier being capable of at least partial o absorption by tissues so as to carry the ascorbic acid and beta-carotene to sub-surface tissues. The second aspect also provides a cosmetic substance comprising ascorbic acid and beta-carotene in a cosmetic base carrier.

The present invention in the second aspect also provides a method of manufacturing a substance for external application to surface body tissues, the method comprising the step of mixing ascorbic acid and beta-carotene with an acceptable carrier or excipient, the carrier being capable of at least partial absorption by tissues so as to carry the ascorbic acid and beta-carotene to sub-surface tissues.

The ingredients may be present in the range of 0.01–10 mg land preferably 0.1 to 1.0 mg) per gram of substance in the case of ascorbic acid and in the range of 0.01 10 mg (and preferably 0.1 to 1.0 mg) per gram in the case of beta-carotene.

Other preferred ingredients include biotin in the range 0.005–0.5 mg (and preferably 0.01 to 0.2 mg) per gram and trypsin in the range 10 to 10,000 U (and preferably in the range 100 to 5.000 U) per gram.

A further preferred ingredient is a coloring marker substance which, when the substance is applied externally. indicates the presence of the substance and while remaining visible indicates that the substance has been insufficiently worked into the skin. A suitable marker substance is chlorophyll (e.g. in the range 0.05–5 mg per gram) which provides a green coloring to the substance but which substantially disappears when the substance is worked into the skin. Chlorophyll has been reported as possibly active in assisting wound or lesion healing.

A typical analysis of a substance according to the second aspect, and possibly also according to the first aspect in the case where the substance ingredients are derived from plant matter, is:

| | |
|---|---|
| ascorbic acid | 0.13 mg |
| beta-carotene | 0.31 mg |
| biotin | 0.048 mg |
| trypsin | 1000 U |
| Chlorocresol | about 1 g |
| chlorophyll | 1.4 mg | balance carrier substance with possible inclusion of other active ingredients.

Preferably the substance has a generally neutral pH in the range 6.0 to 8.0. For example, the pH may be in the range 6.5 to 7.5. Analyses have shown a pH in the range 7 to 7.3.

The composition outlined above can be made up in Cetomacrogol cream. This substance has been found to be suitable for application externally to the skin and has been found effective in the treatment of cold sores. The mechanism of the action of the substance has not been determined. The identified constituents of the cream are believed to be important in maintaining normal skin function or in aiding wound healing. For example beta-carotene is a precursor of vitamin A. Vitamin A is needed for growth and differentiation of epithelial tissues. Ascorbic acid ( vitamin C) is required for collagen synthesis. The combination of the beta-carotene and ascorbic acid constituents appears strongly preferred since when they are used individually the resultant substances are significantly less effective than the combined substance. Therefore it is believed that there is a synergistic effect in operation.

The uses of the substances according to the present invention, whether prepared using the plant extract or whether synthesized from synthetic, processed or otherwise derived ingredients is suitable for cosmetic uses, medicinal uses, pharmaceutical uses.

The present invention has been tested and the following examples give basic summaries of tests carried out. However, the present invention is not limited to any of the specific particulars given in the following examples.

EXAMPLE 1

Sprouted wheat grass was treated to yield the juice which was prepared to provide unjointed, dehydrated wheat grass tablets, which were purchased commercially at a health food store. These tablets had been coated or mixed with non-animal tableting aids. The tablets were comminuted and mixed with Cetomacrogol cream (Sorbolene cream) aqueous A.P.F. 79 supplied by McGloin's. This preparation was externally applied to a cold sore which healed effectively in three days compared to the two or more weeks normal healing time for the person who was treated.

EXAMPLE 2

Dried barley grass juice in powder form was mixed with a carrier or excipient and the preparation was applied to multiple surface eruptions. The treated eruptions receded while the untreated eruptions showed no substantial improvement in the same time period.

To a significant extent the cosmetic and medicinal uses of the invention overlap. It has been found that or is postulated that the preferred substances can be effective in the surface or topical treatment of pimples and acne, minor burns including sunburn, eczema, cracked (fissured) skin, chafed nipples, thrush and vaginal itch, psoriasis, tinea, herpes 1, 2, and 3 (cold sores, genital herpes and herpes zoster or shingles), muscle rub, inflamed joints, piles, anal itch, genital warts, contusions, bruises, scalp treatment including hair tonic uses, gum or mouth lesions and ulcers other surface lesions. Apart from direct physical application involving working the substance into the tissues, it is also believed that the substance can be used for preparations for use as a bathing additive or as a wash including as a mouth wash say for treatment of mouth ulcers or lesions.

It has furthermore been found that the substances may be effective in inhibiting colds and influenza when applied to the nasal mucosa externally, i.e. around the sinus area and the base of the nostrils. The application of the substance to these areas has been carried out daily in test subjects over a significant period. The substances are for external use only since internal application, e.g. to the nasal tissues, can cause discomfort and irritation. It is believed that the substances when externally applied are very slowly taken up by the tissues and in fact do reach the nasal mucous tissues but at very low rates due to the method of administration.

Although external application to reach nasal mucous tissues has been found preferred, the substances can however be directly applied to the vaginal and anal mucous tissues.

According to the third aspect of the present invention there is provided a method of treating skin or mucous tissue, blemishes, infections, eruptions or lesions comprising externally applying a substance according to the first or second aspect to the surface area to be treated and working the substance into the tissues at the area to be treated.

Furthermore according to the third aspect there is provided a method of treating colds, influenza or sinus infections comprising externally applying according to the first or second aspect to the exterior surface of the user's nose and working the substance into the surface nasal tissues, and repeating the application of the substance at daily or more frequent intervals.

The wide range of possible fields of use of the substances are believed to indicate the possibility of effective activity being induced or augmented in the immune system. General supply to tissues of several ingredients, including organic and inorganic substances and electrolytes may be effectively supplementing or boosting body defense or immune mechanisms.

I claim:

1. A pharmacologically effective substance for external application, the substance including an extract consisting of a pharmaceutically acceptable and substantially bacteria-free liquid comprising water and substantially only water soluble components from a juice which has been freshly derived from plants at the unjointed stage of plant development, the plants being selected from barley, wheat, oats, rice, rye and other cereal plants,
   (a) the extraction being by a squeezing, crushing and/or grinding process,
   (b) the extraction being carried out under sterile conditions and/or the extract being treated to prevent or inhibit growth, reproduction or activity of contaminating micro-organisms,
   (c) the extract being carried in a pharmaceutically acceptable base carrier or excipient, the carrier preserving the extract against deterioration and being capable of at least partial absorption by tissues so as to carry the extract to sub-surface tissues.

2. A substance as claimed in claim 1 wherein the juice is stabilized within two hours of derivation from the plants, the stabilization consisting of a process selected from:
   (i) the process of extracting the juice to provide a concentrated liquid comprising said water soluble components in water, and
   (ii) the process of blending the juice with a preserving agent.

3. A substance as claimed in claim 1 wherein the carrier is a water based carrier capable of carrying said water soluble components to sub-surface tissues when applied to a user's skin.

4. A substance as claimed in claim 2 wherein the carrier is a water based carrier capable of carrying said water soluble components to sub-surface tissues when applied to a user's skin.

5. A substance as claimed in claim 2 wherein the substance is maintained in a pH range of 6.0 to 8.0.

6. A substance as claimed in claim 1 wherein the anti-microbial agent is present in the pharmaceutically acceptable base carrier or excipient.

7. A substance as claimed in claim 1 which includes ascorbic acid.

8. A substance as claimed in claim 7 wherein the ascorbic acid is present in proportion of 0.1 to 10 mg per gram of the substance.

9. A substance as claimed in claim 8 and further including biotin present in the range of 0.01 to 0.5 mg per gram of the substance.

10. A substance as claimed in claim 8 and further including trypsin present in the range of 100 to 10,000 U per gram of the substance.

* * * * *